(12) United States Patent
Gerner et al.

(10) Patent No.: US 8,800,800 B2
(45) Date of Patent: Aug. 12, 2014

(54) CARRIER PLATE AND TRANSPORTING AND/OR STORING DEVICE FOR PHARMACEUTICAL CONTAINERS

(71) Applicant: Schott Schweiz AG, St. Gallen (CH)

(72) Inventors: Sebastian Gerner, St. Gallen (CH); Bastian Fischer, St. Gallen (CH)

(73) Assignee: Schott Schweiz AG, St. Gallen (CH)

( * ) Notice: Subject to any disclaimer, the term of this patent is extended or adjusted under 35 U.S.C. 154(b) by 0 days.

(21) Appl. No.: 14/030,687

(22) Filed: Sep. 18, 2013

(65) Prior Publication Data

US 2014/0014654 A1 Jan. 16, 2014

Related U.S. Application Data

(63) Continuation of application No. PCT/EP2012/001095, filed on Mar. 12, 2012.

(30) Foreign Application Priority Data

Mar. 18, 2011 (DE) .......................... 10 2011 104 300

(51) Int. Cl.
*B01L 9/06* (2006.01)
*B65D 1/36* (2006.01)

(52) U.S. Cl.
CPC .... *B01L 9/06* (2013.01); *B65D 1/36* (2013.01)
USPC ...................................... 220/507; 211/71.01

(58) Field of Classification Search
CPC ............ B65D 25/04; B65D 1/42; B65D 1/36; B65D 1/34; A61J 1/16; A61J 1/14; B01L 9/06
USPC ......... 220/516, 509, 507, 628, 669, 608, 623; 211/74, 71.01
See application file for complete search history.

(56) References Cited

U.S. PATENT DOCUMENTS

D98,200 S * 1/1936 Worthington .................. D3/311
3,643,812 A 2/1972 Mander et al.
(Continued)

FOREIGN PATENT DOCUMENTS

EP 1 449 551 A1 8/2004
EP 2 476 448 A1 7/2012
(Continued)

OTHER PUBLICATIONS

Notification of Transmittal of Translation of the International Preliminary Report on Patentability and translation of Written Opinion of the International Searching Authority dated Mar. 12, 2012 for International Application No. PCT/EP2012/001095 (6 pages).

(Continued)

*Primary Examiner* — Robert J Hicks
(74) *Attorney, Agent, or Firm* — Taylor IP, P.C.

(57) ABSTRACT

A carrier plate for pharmaceutical containers, in particular syringes bottles, or ampoules, includes a receiving region that has a plurality of through-openings for receiving the pharmaceutical containers. The receiving region includes a handling region that defines a base plane for handling the carrier plate, in particular for engaging on the carrier plate and/or for supporting same, having a top face that functions as a pressure side under a load and a lower face that functions as a tension side. A structural member for increasing the rigidity of the carrier plate is also provided that includes at least one box profiled region between at least two through-openings on the upper face of the carrier plate.

19 Claims, 6 Drawing Sheets

(56) References Cited

U.S. PATENT DOCUMENTS

| | | | | |
|---|---|---|---|---|
| 5,912,033 | A | * | 6/1999 | Ferguson ..................... 426/124 |
| 6,517,782 | B1 | * | 2/2003 | Horner et al. ................. 422/549 |
| 2006/0266719 | A1 | * | 11/2006 | Knight et al. .................. 211/74 |
| 2008/0282816 | A1 | * | 11/2008 | Dale et al. ................. 73/864.91 |
| 2009/0100802 | A1 | | 4/2009 | Bush et al. |
| 2010/0012546 | A1 | | 1/2010 | Togashi et al. |
| 2012/0103861 | A1 | | 5/2012 | Song et al. |

FOREIGN PATENT DOCUMENTS

| | | | | |
|---|---|---|---|---|
| WO | WO 2008107961 | A1 * | 9/2008 | ................ A61J 1/14 |
| WO | 2011/000606 | A1 | 1/2011 | |

OTHER PUBLICATIONS

International Search report dated Aug. 6, 2012 for International Application No. PCT/EP2012/001095 (4 pages).

* cited by examiner

CARRIER PLATE AND TRANSPORTING AND/OR STORING DEVICE FOR PHARMACEUTICAL CONTAINERS

CROSS REFERENCE TO RELATED APPLICATIONS

This is a continuation of PCT application No. PCT/EP2012/001095, entitled "CARRIER PLATE AND TRANSPORTING AND/OR STORING DEVICE FOR PHARMACEUTICAL CONTAINERS", filed Mar. 12, 2012, which is incorporated herein by reference.

BACKGROUND OF THE INVENTION

1. Field of the Invention

The present invention relates to a transport and/or storage device for pharmaceutical containers.

2. Description of the Related Art

For effective production of pharmaceutical containers, in particular syringes such as pre-fillable syringes, vials or ampoules, that are preassembled in a predefined configuration—so called nests—and are held defined in their position relative to each other and are thereby subjected together and/or simultaneously to the respectively required production processes. The transport and storage of the pharmaceutical containers to/from the devices carrying out the individual production processes, as well as positioning within these devices also occurs in these predefined configurations. For this purpose the pharmaceutical containers are held and stored in a receptacle in the form of a carrier plate, in a defined position relative to each other and relative to the carrier plate. This ensures simultaneous production of a high number of such pharmaceutical containers in one production process. The pharmaceutical containers are individually suspended in receiving openings, in particular in through-openings in carrier plates, are anchored or otherwise positioned therein, in order to protect the containers from damage during transport, and to ensure simultaneous further processing of the entire container configuration. Such predefined configurations with central alignment of the individual containers in the respective through-openings serve in particular to simplify of the collective further processing of the arrangement in predefined process steps, for example sterilization of the containers, filling of the containers, collective safe transport to and from the respective processing devices, closing of the containers, etc. Collective further processing of such an arrangement, in particular filling and closing of the pharmaceutical containers may, for example, occur in a device as described in international publication WO 2011/000606 A1, wherein the arrangement of the pharmaceutical containers undergoes the individual process steps held in place by a carrier plate.

Such carrier plates comprise a receiving region that has a plurality of through-openings to accommodate pharmaceutical containers, a handling region which defines a base plane for handling the carrier plate and/or supporting same, comprising a top side which functions as a pressure side under load, and an under side which functions as a tension side, and a means for increasing the rigidity of the carrier plate. As a rule, the carrier plate is manufactured of plastic. The carrier plate with the pharmaceutical containers positioned and centered therein is however subjected to a multitude of stresses during the aforementioned production and transport processes which lead to undesirable deformations of the carrier plate and which considerably impair handling of the carrier plate, as well as the quality of the production processes. In particular, irreversible cold deformations can be observed on the carrier plate due to the manipulation processes which are to be conducted automatically on the carrier plate to realize the aforementioned production processes. An additional substantial disadvantage is that a secure manual handling of carrier plates containing pharmaceutical containers is not assured due to the low rigidity of the carrier plates. Due to deflection caused under load and the therewith associated positional shift of the pharmaceutical containers relative to each other and in relation to the additional processing device, the filling height when filling the containers and/or the stopper placement height during closing can vary. Warping due to undefined storage conditions and air entrapments during placement of stoppers can also not be ruled out. The defect rate is therefore relatively high, leading either to the inability to use the affected pharmaceutical containers or in a desire to avoid such problems, leading to a disproportionate control system expenditure and/or provision of additional measures for handling.

What is needed in the art is a carrier plate for pharmaceutical containers of the type described above, so that the aforementioned disadvantages are avoided, the manual and also the automated handling of the preassembled arrangement is clearly improved and the defect rate is reduced.

SUMMARY OF THE INVENTION

The present invention provides carrier plates for pharmaceutical containers, such as syringes, vials or ampoules, including a receiving region that has a plurality of through-openings to accommodate pharmaceutical containers, a handling region which defines a base plane for handling the carrier plate, for example, for holding the carrier plate for transport and additional processing purposes and/or supporting of same, a top side which functions as a pressure side under load, an under side which functions as a tension side, and a structural member for increasing the rigidity of the carrier plate is inventively characterized in that the structural member for increasing the rigidity includes at least one box profile region between at least two through-openings on the top side of the carrier plate.

The term "through-opening" is understood to mean an opening configured for a specific functional purpose. This relates to all geometric forms describing through-openings which are suitable to accommodate the pharmaceutical containers in the sense of a through-opening and depending on the specific configuration to hold the pharmaceutical containers through traction and/or form fit, for example, clamping or suspension in a predefined position in or respectively on the carrier plate. Depending on a specific requirement, the through-opening can be formed to have a constant cross section or a changeable cross section in the direction of insertion. Determination of the location of the individual through-openings, as well as the positioning of the individual through-openings relative to each other, the geometric shape, in particular the selection of the cross sectional geometry and/or the cross sectional profile in the direction of insertion, as well as the layout of the individual through-opening occur based on the desired configuration, in particular packing density and geometric design and layout of the pharmaceutical containers which are to be accommodated.

The pressure side is that side of the carrier plate which absorbs the weight of the pharmaceutical containers when these are placed in the carrier plate, and which is thereby subject to bending. The tension side is the side located opposite the pressure side of the carrier plate.

The provision of at least one box profiled region according to the present invention increases the flexural rigidity and torsional stiffness considerably in this arrangement region and thereby ensures secure positioning of the location of the pharmaceutical containers in this region relative to each other and relative to the carrier plate.

For this purpose the at least one box-profiled region is open on one side toward the tension side of the carrier plate. To provide the box profile which stiffens the carrier plate, the center area located opposite the tension side and describing the box profile is arranged, for example, parallel and raised relative to the base plane and coupled with the base plane through webs that form a surface area. In addition to raising the stability of the carrier plate by increasing the flexural rigidity and torsional stiffness, the box profile can be produced cost effectively with only a little more material use, if any. The maximum external dimensions of the carrier plate in a horizontal plane are thereby unaffected.

Regarding configuration and layout of the individual box profile region there are a multitude of possibilities. In order to ensure high stability, the at least one box profile region is however always located in the region of the theoretical maximum deflection of the carrier plate. The deflection curve of the loaded carrier plate can thereby be considerably flattened.

According to an embodiment of the present invention, the structural member for increasing rigidity can include a multitude of box profile regions that are open on one side toward the tension side of the carrier plate and are coupled via connecting regions which are located across the base plane or offset to same and are arranged between at least two or more adjacently located through-openings. In this case the rigidity is achieved through a multitude of individual box profile modules and their configuration. A configuration of this type can be useful with necessary provision of additional function elements.

In another embodiment the structural member for increasing rigidity includes only one box profile region forming a box module between all through-openings, which is open on one side toward the tension side of the carrier plate. This describes a grid-like structure which is arranged extending between the individual through-openings. This solution offers the advantage of simple production and at the same time very high achievable flexural rigidity and torsional stiffness of the carrier plate across the entire receiving region for pharmaceutical containers.

To increase the functional concentration, a single box profile region which is open toward the tension side of the carrier plate forms at least also one partial region of a wall of at least one through-opening in an advancement of the present invention. This solution can be realized easily with a single component form of the entire carrier plate in the embodiment of an injection molded component.

In an additional advancement of the present invention, the structural member for increasing the rigidity includes ribs located on the tension side of the carrier plate, connecting always two adjacent through-openings to further increase rigidity. In a further variation of the present invention these ribs are located in the region of the base plane, for example within a single box profile region. Thereby one version of the carrier plate is realized which is only very slightly enlarged in height direction compared to the current state of the art.

There are basically no restrictions in regard to the selection of material for the carrier plate. However, in view of the production process of the more complex geometries and characteristics, plastic materials may be used. For example polypropylene and polyester are exemplary materials used in this application.

In a time saving and economically producible arrangement, the carrier plate is formed as an integral unit, for example as an injection molded component with all its parts. This offers the advantage that the box profile region and the additional structural member for increasing rigidity can be produced also in more complex geometries precisely and in a simple manner.

If, in an alternative variation of the present invention, the carrier plate is formed as a multi-component unit, there is the possibility of retrofitting the structural member to increase the rigidity in conventional carrier plates by linking the box profile regions by frictional and/or material bonding to the through-openings and the respective base plane.

To avoid twisting of pharmaceutical containers which have been inserted into the through-openings of the carrier plate it may be provided that the carrier plate is equipped with a device to prevent twisting of the individual pharmaceutical containers which have been inserted into the through-openings. In one variation the device may include webs crossing each other which are arranged on the top side of the carrier plate, in particular in the region of the box profile between adjacent through-openings. Even though the described inventive variation refers to webs crossing each other for the anti-twist protection device, this type of arrangement is not obligatory. All arrangements which include, for example, a stop for a syringe collar in order to thereby avoid twisting of a syringe that has been inserted into a through-opening are conceivable for the expert.

In a further embodiment, the inventive carrier plate can be inserted into a transport and/or storage device for pharmaceutical containers, in particular syringes, vials or ampoules. This includes a storage container in which the carrier plates can be stored, either empty or loaded, and at least one cover for the storage container. Additional elements, for example sealing devices are foreseeable. Due to the high rigidity of the carrier plate itself, the containers stored in the carrier plate remain centered and defined in their positions in the through-opening relative to each other during transportation and storage, even over a longer time period. Damage to the containers can hereby be avoided.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
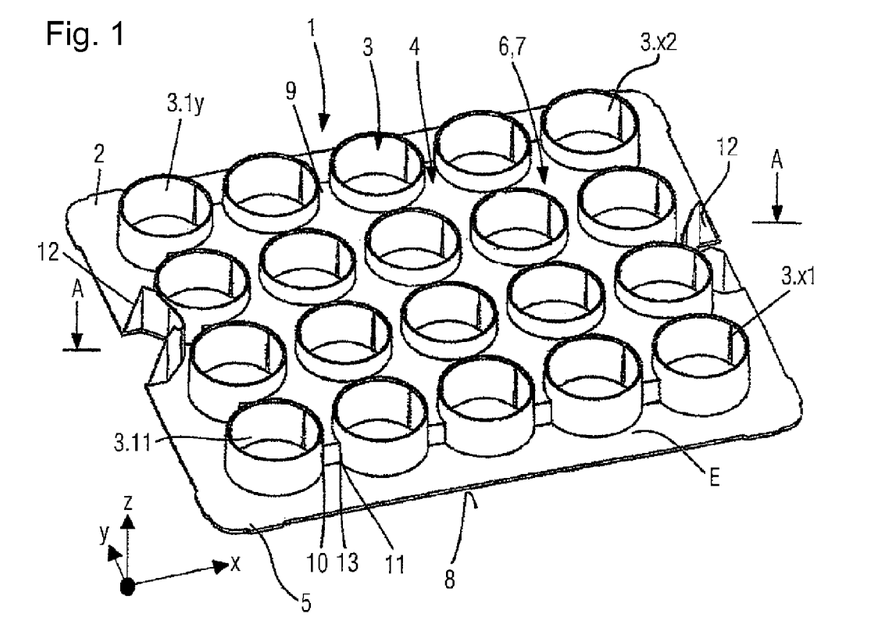
FIG. 1 shows a first embodiment of a carrier plate according to the present invention in a perspective view of the top side.

Referring now to the drawings, and more particularly to FIG. 1, there is shown a perspective view of a first embodiment of a carrier plate 1 according to the present invention for pharmaceutical containers, such as syringe bodies, vials and ampoules which are not illustrated here—the view being top side 2 which functions as the pressure side when accommodating the pharmaceutical containers. In the illustrated example carrier plate 1 is rectangular. This basic shape permits optimum configuration of the containers and favorable handling.

Other basic shapes are also conceivable, however are dependent upon the specific application. For clarification of the individual directions a coordinate system is, for example, applied to carrier plate 1. X-direction indicates the longitudinal direction, Y-direction indicates the width direction, and Z-direction indicates the height direction.

Carrier plate 1 is an integral component in this embodiment, meaning that it is constructed as a single component. It is, for example, manufactured as an injection molded part. Carrier plate 1 includes a receiving region 4 that has a plurality of through-openings 3 to accommodate pharmaceutical containers. The through-openings 3 are arranged here uniformly in rows and columns and are identified with 3.11 to 3.$x$1, 3.1$y$ to 3.$xy$ with x>1, y>1. Other arrangements, uniform or non-uniform are also conceivable. Carrier plate 1 further includes one handling region 5 which defines a base plane E for handling of carrier plate 1, and a structural member 6 for increasing the rigidity of carrier plate 1. According to the present invention, structural member 6 for increasing the rigidity includes at least one box profile region 7 between at least two through-openings 3 on top side 2. Box profile region 7 connects hereby these at least two through-openings 3. The at least one box profile region 7 is formed to be open toward under side 8 which acts as the tension side of carrier plate 1 and is essentially defined by three side surfaces describing a U- or C-profile and the surfaces occluding the profile. The profile cross section is characterized by two side surfaces and one center surface 9 located between them, which is, for example, arranged parallel to base plane E and offset in the height direction to same. Center surface 9 is located opposite the open side of box profile region 7 and can be flat. Conceivable would also be a diagonal progression or a progression which extends like an arched bridge over the area of the box shape. The geometric shape is determined depending on the layout and progression of an individual box profile region 7. Coupling of center region 9 with base plane E occurs through side surfaces 10, 11 which form the webs whose configuration is also determined depending on the arrangement and progression of an individual box profile region 7.

The arrangement of at least one box profile region 7 occurs at least in the range of the theoretical maximum deflection of carrier plate 1. FIG. 1 illustrates an embodiment of box profile region 7, which extends, for example, across the entire receiving region 4. Box profile region 7 in this case forms a box module in a single component form with handling region 5 and in functional concentration also forms walls of through-openings 3.11 to 3.$xy$.

In the illustrated example carrier plate 1 is in the embodiment of a single component injection molded component, whereby the through-openings 3.11 to 3.$xy$ are, for example, shaped during its production. Here, the through-openings 3.11 to 3.$xy$ are characterized by cylindrical elements which are produced with the box module as a single structural unit, whereby a section of the circumferential surface of such a cylindrically shaped element assumes the function of the side surfaces 10, 11 which function as webs. The occlusion in the height direction of box profile region 7 occurs over surfaces 13 that form the webs.

The box module is formed such that box profile 7 formed by it surrounds all interior through-openings completely and through-openings 3.11 to 3.$x$1, 3.11 to 3.1$y$, 3.1$y$ to 3.$xy$ and 3.$x$1 to 3.$xy$ which are respectively arranged in the outer columns and rows at least partially in circumferential direction, whereby the wrap angle for the through-openings located in the outer rows and columns are, for example equal to or greater than 180°. In this area box profile 7 is occluded by surfaces 13 that form the webs between respectively adjacent through-openings in the respective outer columns and rows.

Handling region 5 can be configured depending on the requirements upon the function of carrier plate 1. In the illustrated example, handling region 5 is characterized by a device 12 being provided on both sides which facilitates for example carrier plate 1 being placed in a storage container for transportation purposes and the formation of pick-up areas for transport.

Figure 2:
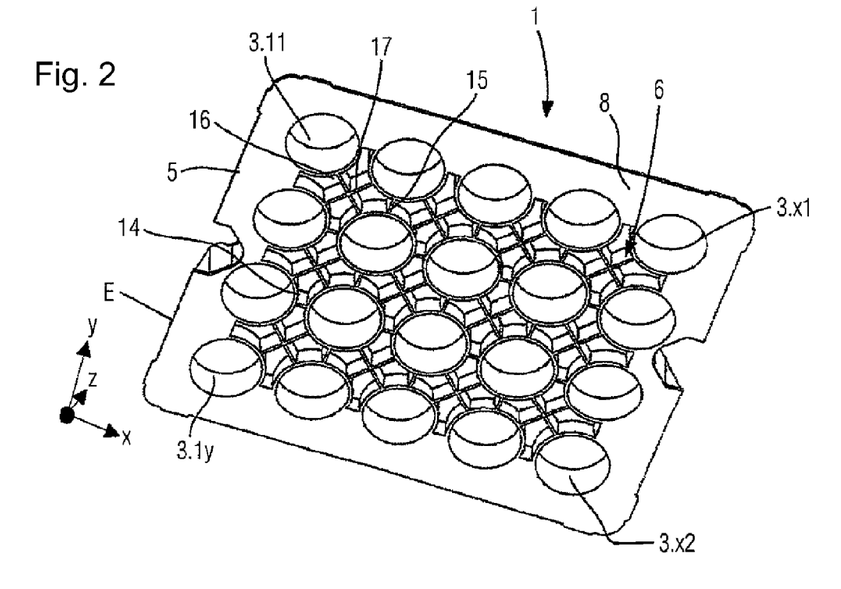
FIG. 2 shows the carrier plate according to FIG. 1 in a perspective view of the underside.

Referring now to FIG. 2, there is shown a perspective illustration of carrier plate 1 illustrated in FIG. 1, showing a view from the bottom onto bottom side 8. Here, structural member 6 may include ribs 14, 15, 16 and 17 arranged on the tension side of carrier plate 1 for increasing the rigidity. Ribs 14 hereby connect the walls forming the individual through-opening of adjacent through-openings, within a row x. Ribs 15 serve to connect the walls forming the individual through-openings of adjacent through-openings in column y. Ribs 16 and 17 serve to connect a through-opening with the additional immediately adjacent through-openings. Ribs 16, 17 are arranged, for example, crossing each other. The placement of ribs 14 to 17 occurs, for example, in the region of base plane E and therefore, in the illustrated arrangement in the region of the open end of box profile region 7. According to one arrangement of the present invention, ribs 14 to 17 are arranged, for example, completely within the extension of box profile region 7 in the height direction and thereby integrated in same. Ribs 14 to 17 thereby always connect through-openings with each other in the region of their outside circumference, whereby ribs 14 to 17 may extend to the wall regions of the through-openings in the direction of the tension side of carrier plate 1.

As already mentioned, carrier plate 1 may be manufactured as a single plastic component as an injection molded component. Fabrication by injection molding allows for very complex stiffening geometries with simple means in only a single process step.

Figure 3:
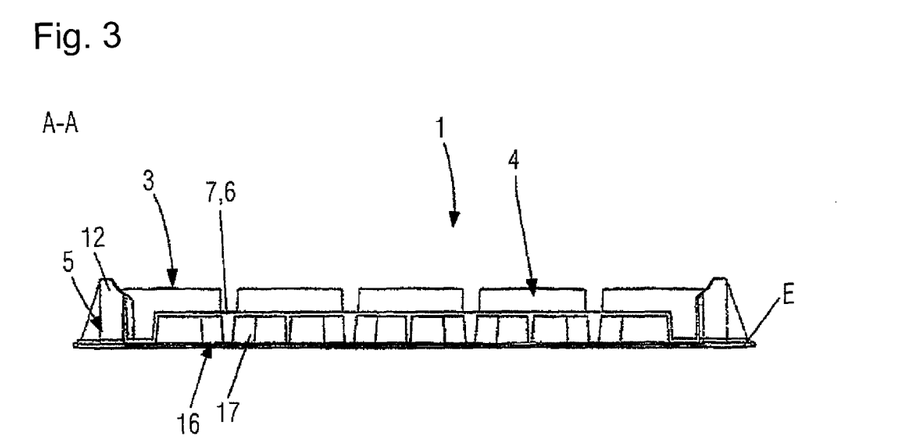
FIG. 3 shows a view A-A according to FIG. 1.

Referring now to FIG. 3, there is shown carrier plate 1 in a sectional view A-A according to FIG. 1. Visible are handling region 5, devices 12 and through-openings 3 and the box module connecting them in the form of box profile region 7. Also shown in this sectional view are ribs 16, 17 connecting the outside circumferences of through-openings 3.

Figure 4:
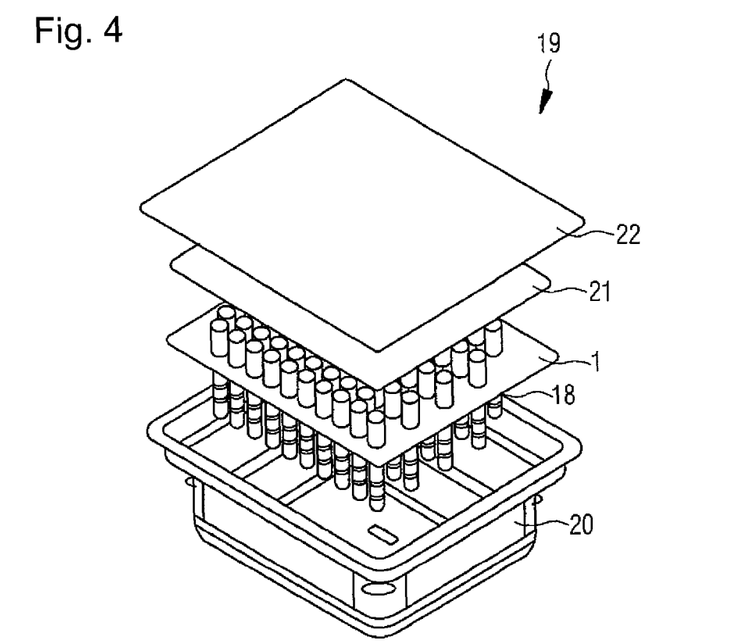
FIG. 4 shows an exploded view of a carrier plate according to the present invention, being inserted into a storage container for transportation purposes.

Referring now to FIG. 4, there is shown an exploded view of an embodiment of carrier plate 1 according to the present invention with containers 18 accommodated in it, shown in a transport and storage device 19, including a tub-like storage container 20. Carrier plate 1 loaded with pharmaceutical containers 18 can be placed into storage container 20 and can, for example be suspended or supported by devices 12 and/or additional devices which would secure the position of carrier plate 1 in tub-like storage container 20. In the illustrated example, a cover plate 21 and a sealing plate 22 for closing storage container 20 are provided which—after storing loaded carrier plate 1—are placed over carrier plate 1, closing off storage container 20.

Support of carrier plate 1 in storage container 20 is realized by friction locking and/or material bonding. The specific choice depends on the individual application. The closure is generally made possible through a cover which can be combined with additional devices, such as a sealing device, insulating materials, etc.

Referring now to FIGS. 5 through 8, there is shown another embodiment of carrier plate 1 according to the present invention. Same components as shown in FIGS. 1 through 4 are identified with numbers which are increased by 1000.

Figure 5:
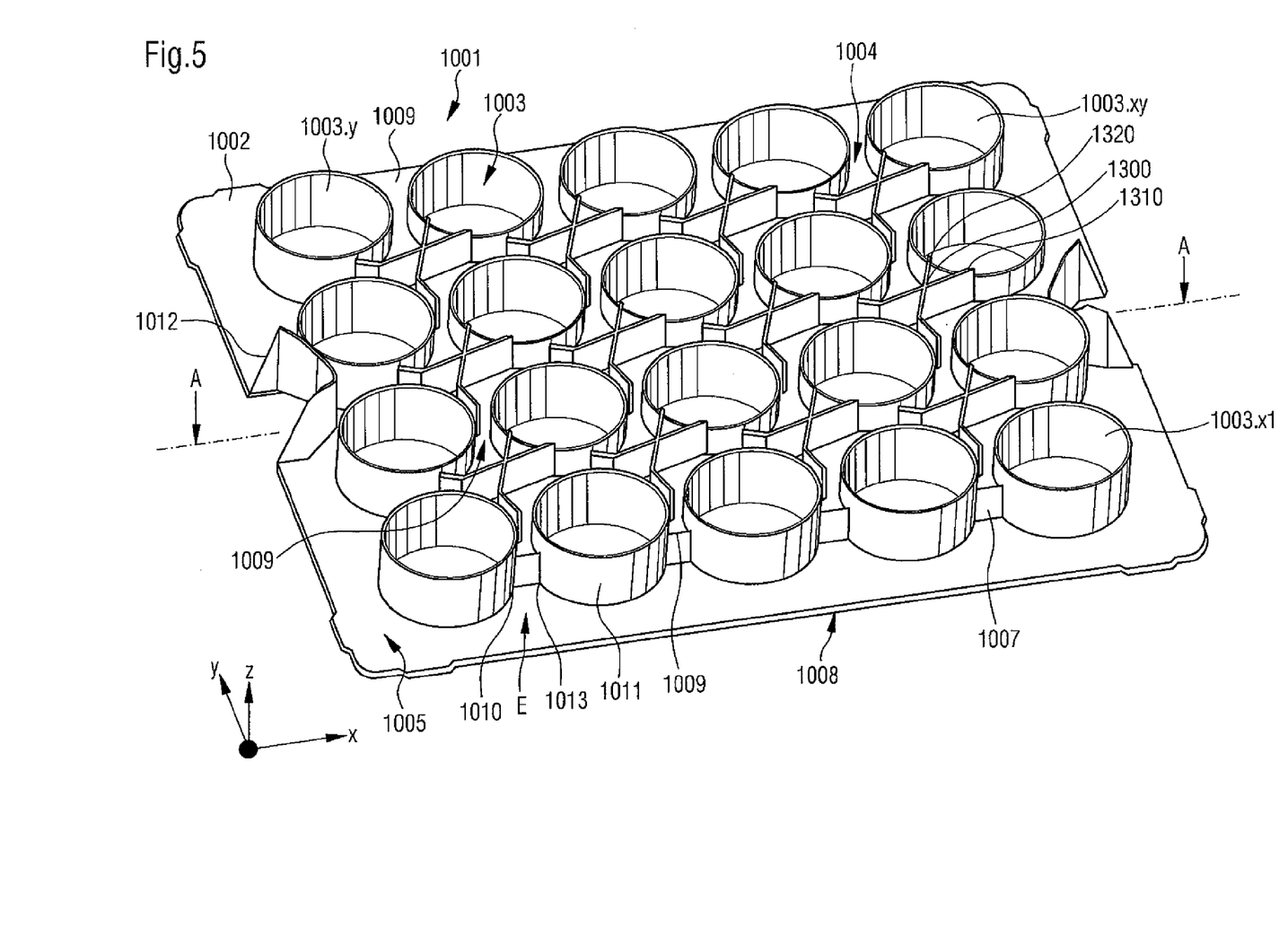
FIG. 5 shows an additional embodiment of a carrier plate according to the present invention in a view of the top side, with an anti-twist device.

Referring now to FIG. 5, there is illustrated in a perspective depiction the second embodiment of carrier plate 1001 according to the present invention for pharmaceutical containers, in particular syringe bodies, vials or ampoules which are not illustrated here—the view being top side 1002 which functions as the pressure side when accommodating the pharmaceutical containers. In the illustrated example, carrier plate 1001 is rectangular.

This basic shape permits optimum configuration of the containers and favorable handling. Other basic shapes are, however, also conceivable and are dependent upon the specific application. For clarification of the individual directions a coordinate system is for example applied to carrier plate 1001. X-direction indicates the longitudinal direction, Y-direction indicates the width direction, and Z-direction indicates the height direction.

Carrier plate 1001 is an integral component in this embodiment, meaning that it is constructed as a single component. It is, for example, manufactured as an injection molded part. Carrier plate 1001 includes a receiving region 4 that has a plurality of through-openings 1003 to accommodate pharmaceutical containers. Through-openings 1003 are arranged here, for example, uniformly in rows and columns and are identified with $1003.11$ to $3.x1$, $1003.1y$ to $1003.xy$ with $x>1$ m $y>1$. Other arrangements, uniform or non-uniform are also conceivable. Carrier plate 1001 further includes one handling region 1005 which defines a base plane E for handling of carrier plate 1001, and structural member 1006 to increase the rigidity of carrier plate 1001. According to the present invention, structural member 1006 for increasing the rigidity includes at least one box profile region 1007 between at least two through-openings 1003 on top side 1002. Box profile region 1007 connects hereby these at least two through-openings 1003. The at least one box profile region 1007 is formed to be open toward under side 1008 which acts as the tension side of carrier plate 1001 and is essentially defined by three side surfaces describing a U- or C-profile and the surfaces occluding the profile. The profile cross section is characterized by two side surfaces and one center surface 1009 located between them, which is, for example, arranged parallel to base plane E and offset in the height direction to same. Center surface 1009 is located opposite the open side of box profile region 1007 and is, for example flat. The geometric shape is determined depending on the layout and progression of an individual box profile region 1007. Coupling of center surface region 1009 with base plane E occurs through the surfaces 1010, 1011 which form the webs whose configuration is also determined depending on the arrangement and progression of individual box profile region 1007.

The arrangement of the at least one box profile region 1007 occurs at least in the range of the theoretical maximum deflection of carrier plate 1001. FIG. 1 illustrates an embodiment of a box profile region 1007, which extends, for example, across the entire receiving region 1004. Box profile region 7 in this case forms a box module in a single component form with handling region 1005 and in functional concentration also forms walls of through-openings $1003.11$ to $1003.xy$.

In the illustrated example carrier plate 1001 is in the embodiment of a single component injection molded component, whereby through-openings $1003.11$ to $3100.xy$ are, for example, shaped during its production. Here, through-openings $1003.11$ to $1003.xy$ are characterized by cylindrical elements which are produced with the box module as a single structural unit, whereby a section of the circumferential surface of a thus formed element assumes the function of the side surfaces 1010, 1011 which function as webs. The occlusion in the height direction of box profile region 1007 occurs over surfaces 1013 forming the webs.

The box module is formed such that box profile 1007 formed by it surrounds all interior through-openings completely and through-openings $1003.11$ to $1003.x1$, $1003.11$ to $1003.1y$, $1003.1y$ to $1003.xy$ and $1003.x1$ to $1003.xy$ which are respectively arranged in the outer columns and rows at least partially in a circumferential direction, whereby the wrap angle for the through-openings 1003 located in the outer rows and columns are, for example, profile 1007 is occluded by surfaces 1013 forming the webs between respectively adjacent through-openings in the respective outer columns and rows.

Handling region 1005 can be formed depending on the requirements upon the function of carrier plate 1001. In the illustrated example the handling region is characterized by devices 1012 being provided on both sides which facilitate, for example, carrier plate 1001 being placed in a receptacle for transportation purposes and formation of pick-up areas for transport.

In addition to the first embodiment in FIGS. 1 to 4, the second embodiment of the present invention is equipped with an anti-twist protection device 1300 between adjacent through-openings 1003. In this embodiment, anti-twist protection device 1300 is formed by two crosspieces 1310, 1320 which are crossed. Crosspieces 1310, 1320 of anti-twist protection device 1300 are arranged on center surface 1009 in box profile region 1007. In addition to ribs 1014, 1015, 1016, 1017 on bottom side 1008 of carrier plate 1001, crosspieces 1310, 1320 of anti-twist protection device 1300 also assumes a strengthening function. Moreover, crosspieces 1310, 1320 are formed and arranged such that they assume an anti-twist protection of the pharmaceutical containers, in particular fillable syringes, vials or ampoules which are inserted in through-openings 1003. Thereby not only a predetermined position of the pharmaceutical containers relative to each other can be maintained, but also the position of the angle of the pharmaceutical containers which are inserted in the, for example, rotationally symmetrical through-opening 1003. This is shown in detail for syringes in FIG. 8. Crosspieces 1310, 1320 are adapted exactly to the pharmaceutical containers inserted in through-opening 1003. The anti-twist protection serves to avoid twisting of the pharmaceutical containers in handling region 1005, in particular in the region of devices 1012. This is of particular importance if no manual handling feature is available on device 1012 and only mechanical handling is provided, for example whereby centering pins engage in device 1012. If, in a mechanically processed unit, for example a syringe twists or rotates out of the predefined angle position due to missing anti-twist protection, then the area of device 1012 could be covered. A mechanical handling is then no longer possible and the process reliability is impaired.

Figure 6:
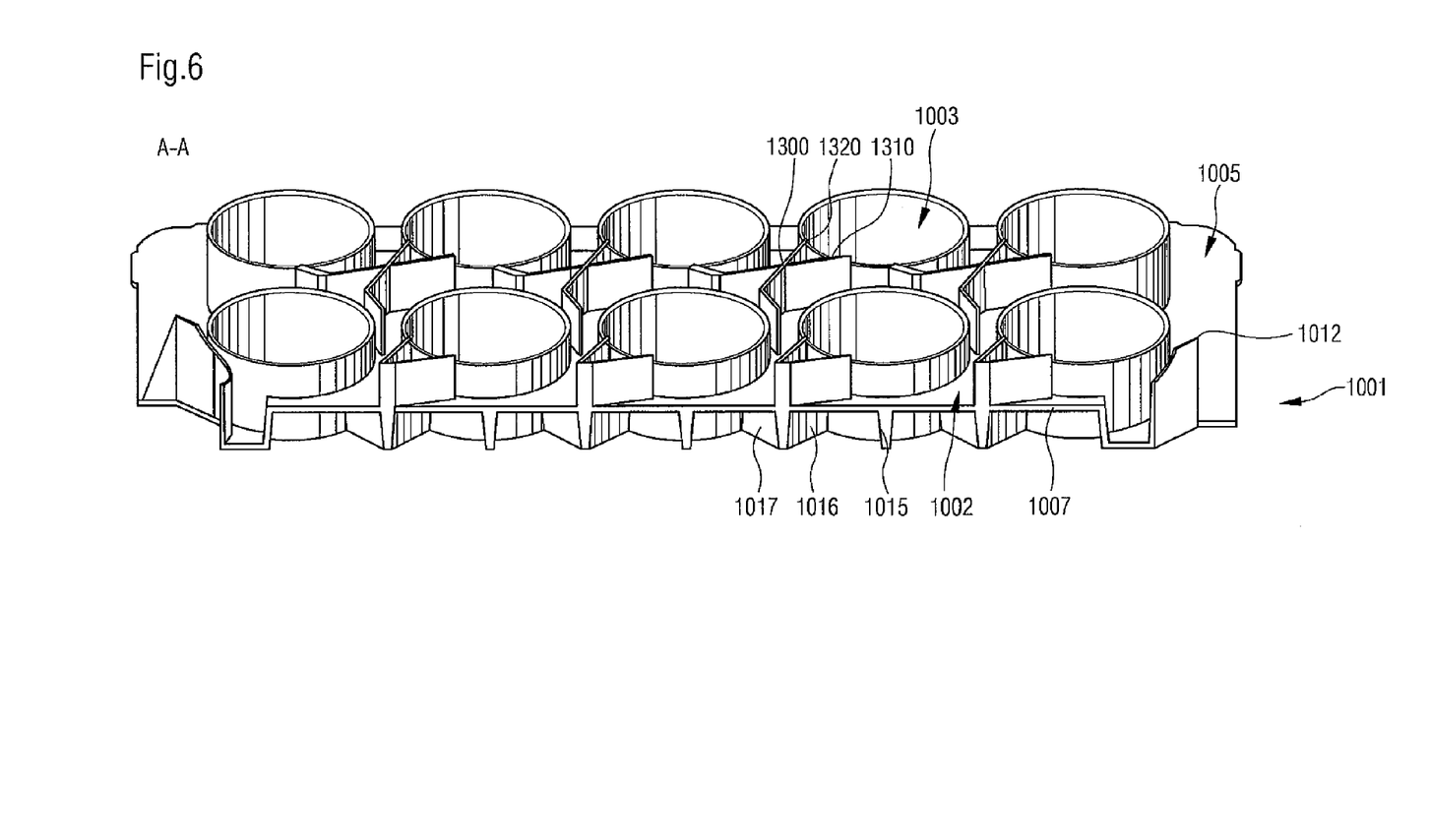
FIG. 6 shows a detail of the carrier plate according to FIG. 5 in sectional view with box profile region and an anti-twist device along section A-A.

Referring now to FIG. 6, there is shown a perspective illustration of a sectional top view of carrier plate 1001, which is illustrated in FIG. 5. In section A-A in FIG. 5 it can be clearly seen that structural member 1006 for increasing the rigidity on the tension side of carrier plate 1001 includes ribs 1014, 1015, 1016 and 1017. Ribs 1014 (not illustrated) analogous to rib 14 in FIG. 2 connect the individual through-opening forming walls of adjacent through-openings within a row x. Ribs 1015 serve to connect the walls forming the individual through-openings 1003 of adjacent through-openings in a column y. Ribs 1016 and 1017 serve to connect a through-opening 1003 with the additional immediately adjacent through-openings 1003. Ribs 1016, 1017 are, for example, arranged crossing each other. The placement of ribs 1014 to 1017 occurs, for example, in the region of base plane E and therefore, in the illustrated arrangement in the region of open end of box profile region 1007. According to one arrangement, ribs 1014 to 1017 are arranged, for example, completely within the extension of box profile region 1007 in the height direction and thereby integrated in same. Ribs 1014 to 1017 thereby always connect through-openings with each other in the region of the outside circumference, whereby ribs 1014 to 1017 may extend to the wall regions of the through-openings in the direction of the tension side of carrier plate 1001.

As already mentioned, carrier plate 1001 is, for example, manufactured as a single plastic component such as an injection molded component. Fabrication by injection molding allows for very complex stiffening geometries with simple means in only a single process step.

Figure 7:
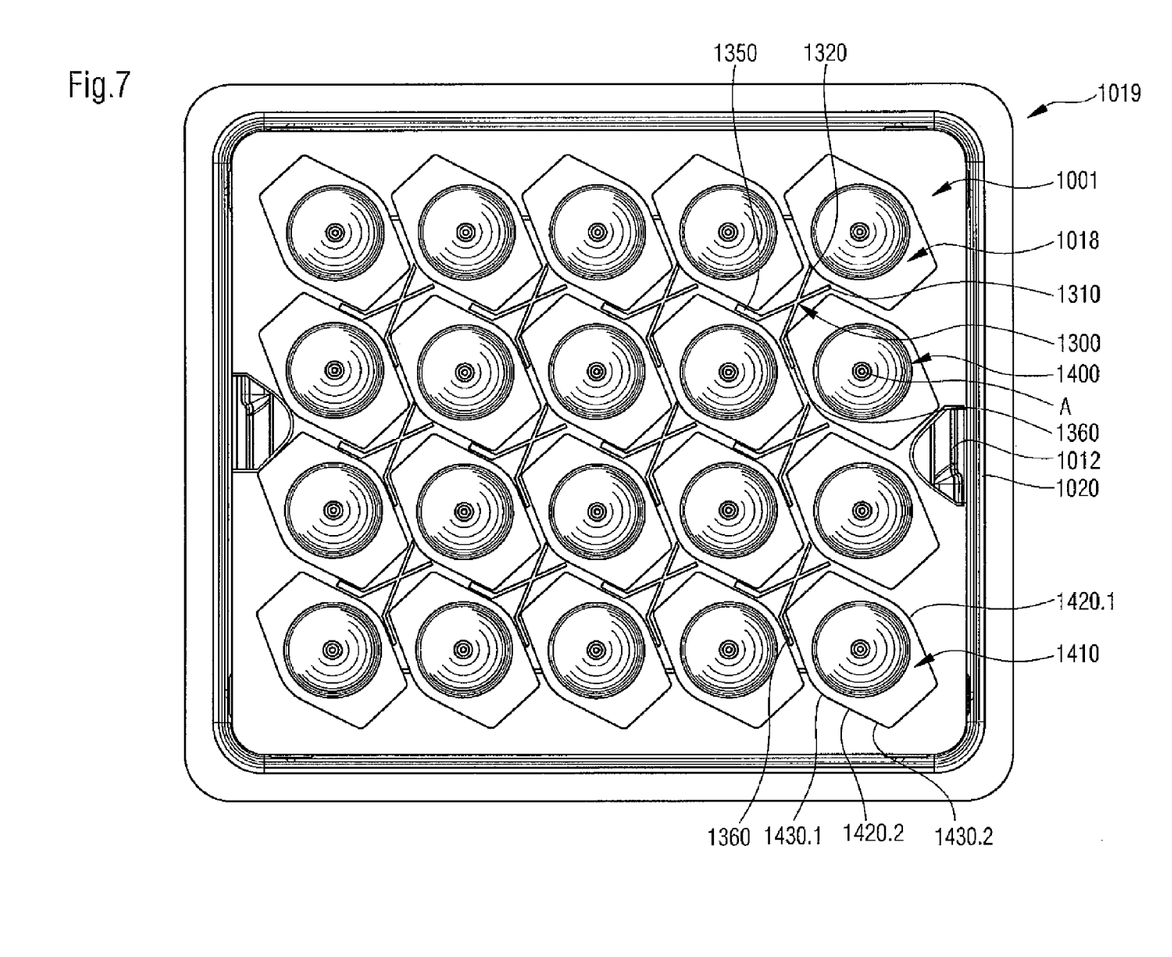
FIG. 7 shows a top view of the second embodiment of a carrier plate according to FIG. 5 with inserted pharmaceutical containers, in particular syringes.
Figure 8:
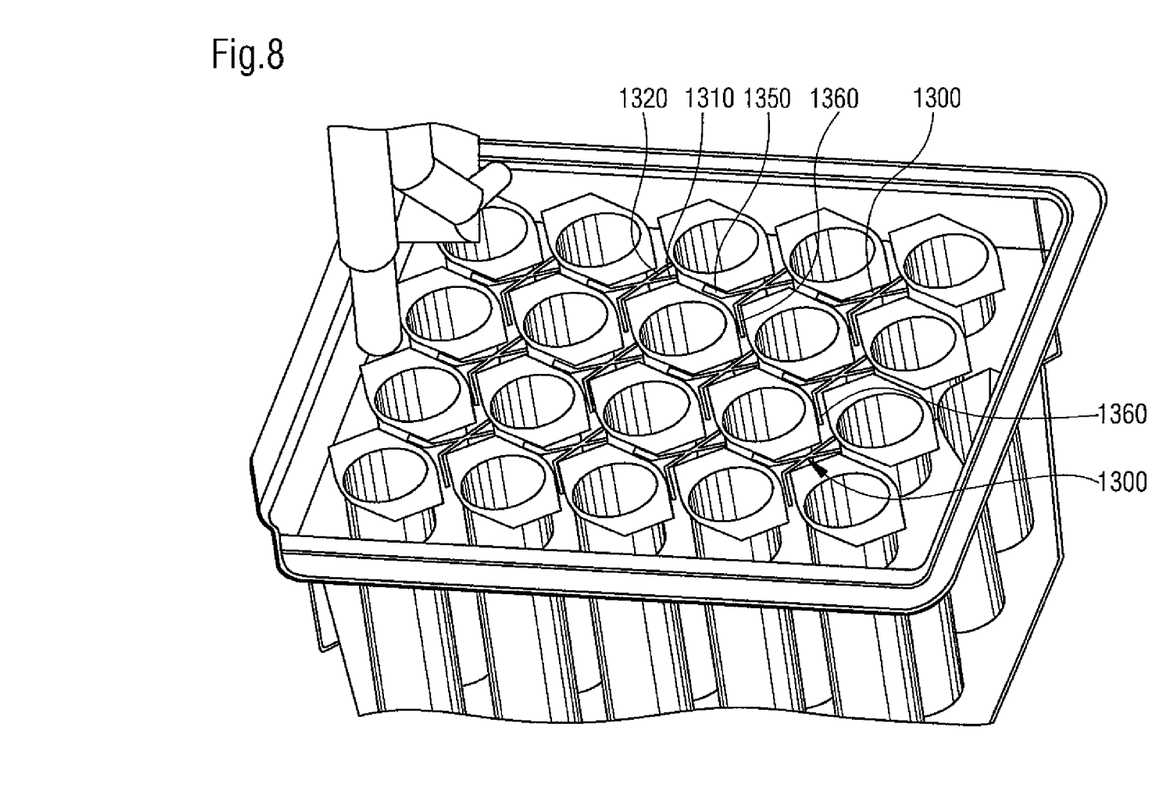
FIG. 8 shows a three-dimensional view of a variation of the carrier plate according to FIG. 5 with inserted pharmaceutical containers, in particular syringes.

Referring now to FIG. 7, there is shown a second embodiment of carrier plate 1001 with pharmaceutical containers 1018 accommodated in it, shown in a top view of transport and storage device 1019, including a tub-like storage container 1020 as illustrated in detail in FIG. 8. Carrier plate 1001 loaded with pharmaceutical containers 1018—in this example syringe bodies 1400—can be brought into receptacle 1020 and can, for example be suspended or supported by devices 1012 and/or additional devices which would secure the position of carrier plate 1001 in tub-like storage container 1020. A cover plate and a sealing plate for closing receptacle 1020 can be provided which—after storing the loaded carrier plate 1001—are placed over carrier plate 1001, closing off the receptacle.

Support of carrier plate 1001 in the storage container is realized by friction locking and/or material bonding. The specific choice depends on the individual application. The closure is generally made possible through a cover which can be combined with additional functional devices, such as a sealing device, insulating materials, etc.

Devices 1300 for anti-twist protection, including cross pieces 1310, 1320 can be clearly seen in FIG. 7. The individual syringe bodies include a syringe collar 1410 having two respective side regions 1420.1, 1420.2, including two respective side regions 1430.1, 1430.2. Crosspieces 1310, 1320 each have a stop segment 1350, 1360, which fit closely against a side region 1430.1, 1430.2 of the syringe collar. The close fit of at least one stop segment 1350, 1360 against at least one side region 1430.1, 1340.2 of a syringe collar of a syringe body can prevent the syringe from rotating around its axis A or respectively the axis of the through-opening, in other words that it is moved out of its angular position and thereby, for example, unintentionally covers regions 1012.

Referring now to FIG. 8, there is shown a three-dimensional view of an embodiment of a carrier plate 1001, inserted in a tub-like storage container. Same components as in FIG. 7 are identified with the same reference numbers. Clearly visible is syringe body 1400 with syringe collar 1410 and cylindrical syringe segment 1440 which can be filled, for example with a pharmaceutical product or another fluid, and be inserted in a through-opening 1001.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

COMPONENT IDENTIFICATION LIST

1, 1001 carrier plate
2, 1002 top side
3, 3.11-3.$x$1 through-openings
3.1$y$-3.$xy$
1003, 1003.11—
1003.$x$1, 100.1—
1003.$xy$
4, 1004 receiving region
5, 1005 handling region
6, 1006 structural member for increasing rigidity
7, 1007 box profile region
8, 1008 bottom side
9, 1009 center area
10, 1010 side surface
11, 1011 side surface
12, 1012 device
13, 1013 surface
14, 1014 rib
15, 1015 rib
16, 1016 rib
17, 1017 rib
18, 1018 pharmaceutical containers
19, 1019 transport and storage device
20, 1020 storage container
21 cover plate
22 sealing plate
1300 device for anti-twist protection
1310, 130 crosspieces of the device for anti-twist protection
1350, 1360 stop segment for cross piece
1400 syringe body
1410 syringe collar
1420.1, 1420.2 long sides
1430.1, 1430.2 side segments
1440 syringe segment

What is claimed is:

1. A carrier plate for pharmaceutical containers, the carrier plate comprising:
   a receiving region having a plurality of through openings configured to accommodate the pharmaceutical containers;
   a handling region which defines a base plane for handling the carrier plate;
   a top side operating as a pressure side under load;

an under side operating as a tension side; and a structural member for increasing a rigidity of the carrier plate, said structural member including at least one box profile region between at least two of said plurality of through openings on said top side of the carrier plate.

2. The carrier plate according to claim 1, said handling region being configured for handling the carrier plate for at least one of transport, additional processing and support.

3. The carrier plate according to claim 1, wherein said at least one box profile region is open on one side in a direction toward said tension side of the carrier plate and a center area located opposite said tension side and describing said box profile is arranged parallel and raised relative to a base plane and coupled with said base lane through a plurality of webs that form a plurality of surface areas.

4. The carrier plate according to claim 3, wherein said at least one box profile region is located at least in a region of a theoretical maximum deflection of the carrier plate.

5. The carrier plate according to claim 4, said structural member for increasing rigidity including a multitude of said box profile regions open in said direction toward said tension side of the carrier plate and coupled via a plurality of connecting regions located across said base plane or offset to said base plane and are arranged between at least two or more adjacently located said through openings.

6. The carrier plate according to claim 4, said structural member for increasing rigidity including one said box profile region forming a box module between all of said through openings, said box module being open on a side in a direction toward said tension side of the carrier plate.

7. The carrier plate according to claim 6, wherein said single box profile region forms at least one partial region of a wall of at least one of said through-openings.

8. The carrier plate according to claim 7, said structural member for increasing rigidity including a plurality of ribs located on said tension side of the carrier plate and connecting always two adjacent said through openings.

9. The carrier plate according to claim 8, said ribs being arranged within a vertical extension of said single box profile region.

10. The carrier plate according to claim 1, wherein the carrier plate is an integral component.

11. The carrier plate according to claim 10, the carrier plate being an integral injection molded component.

12. The carrier plate according to claim 1, said receiving region and said handling region of the carrier plate being an integral component.

13. The carrier plate according to claim 12, wherein said receiving region and said handling region are an integral injection molded component and said individual box profile region is connected with said integral injection molded component through at least one of friction locking and material bonding.

14. The carrier plate according to claim 1, further comprising a plurality of devices for anti-twist protection.

15. The carrier plate according to claim 14, wherein said devices for anti-twist protection include a plurality of cross-pieces.

16. The carrier plate according to claim 15, said cross-pieces including at least one stop segment.

17. The carrier plate according to claim 16, said at least one stop segment being a stop segment for a syringe collar.

18. A transport and storage device for a plurality of pharmaceutical containers, the transport and storage device comprising:

a carrier plate, including:

a receiving region having a plurality of through openings configured to accommodate the pharmaceutical containers;

a handling region which defines a base plane for handling the carrier plate;

a top side operating as a pressure side under load;

an under side operating as a tension side; and a structural member for increasing a rigidity of the carrier plate, said structural member including at least one box profile region between at least two of said plurality of through openings on said top side of the carrier plate;

a storage container, said storage container and said carrier plate configured for being stored in a defined position in said storage container; and at least one cover plate for closing said storage container.

19. The transport and storage device according to claim 18, configured for transporting and storing one of syringes, vials and ampoules.

* * * * *